United States Patent [19]

Mickael

[11] Patent Number: 5,789,752
[45] Date of Patent: Aug. 4, 1998

[54] THERMAL NEUTRON POROSITY MEASUREMENT APPARATUS AND METHOD USING AN ACCELERATOR TYPE HIGH-ENERGY NEUTRON SOURCE

[75] Inventor: Medhat W. Mickael, Sugar Land, Tex.

[73] Assignee: Western Atlas International, Inc., Houston, Tex.

[21] Appl. No.: 935,117

[22] Filed: Sep. 22, 1997

Related U.S. Application Data

[63] Continuation-in-part of Ser. No. 763,128, Dec. 11, 1996, abandoned, which is a continuation-in-part of Ser. No. 651,728, May 22, 1996, abandoned.

[51] Int. Cl.[6] .................................................. G01V 5/10
[52] U.S. Cl. .................................. 250/269.5; 250/269.4
[58] Field of Search ........................... 250/269.4, 269.5, 250/262, 264, 265, 266

[56] References Cited

U.S. PATENT DOCUMENTS

| | | | |
|---|---|---|---|
| 2,914,677 | 11/1959 | Arnold | 250/269.5 X |
| 3,529,160 | 9/1970 | Moran | 250/262 |
| 3,621,255 | 11/1971 | Schwartz | 250/262 X |
| 3,823,319 | 7/1974 | Tittman | 250/269.5 X |
| 4,005,290 | 1/1977 | Allen | 250/269.5 X |
| 4,122,340 | 10/1978 | Smith, Jr. et al. | 250/269.5 X |

*Primary Examiner*—Edward J. Glick
*Attorney, Agent, or Firm*—Richard A. Fagin

[57] ABSTRACT

An apparatus for measuring the porosity of earth formations penetrated by a wellbore. The apparatus includes an elongated housing adapted to traverse the wellbore, a controllable source which emits bursts of high-energy neutrons, a near detector primarily sensitive to thermal neutrons and axially spaced apart from the source, a far detector also primarily sensitive to thermal neutrons and axially spaced apart from the source so that the near detector is axially disposed between the source and the far detector. The apparatus includes a neutron shield disposed between the near detector and the far detector, and a neutron scattering insert disposed inside the housing between the source and the near detector. The scattering insert consists of a material selected from the group of aluminum, beryllium, graphite, silicon, potassium, magnesium, lead and sulfur. In a preferred embodiment, the scattering insert consists of aluminum.

17 Claims, 16 Drawing Sheets

5,789,752

THERMAL NEUTRON POROSITY MEASUREMENT APPARATUS AND METHOD USING AN ACCELERATOR TYPE HIGH-ENERGY NEUTRON SOURCE

CROSS REFERENCE TO RELATED APPLICATIONS

Continuation-in-part of application Ser. No. 08/763,128 filed on Dec. 11, 1996, assigned to the assignee of this invention and now abandoned, which is itself a continuation-in-part of application Ser. No. 08/651,728 filed on May 22, 1996 now abandoned, assigned to the assignee of this invention and now abandoned.

BACKGROUND OF THE INVENTION

1. Field of the Invention

The invention is related to the field of radioactive well logging apparatus and methods. More specifically, the invention is related to apparatus and methods for measuring thermal neutron porosity of earth formations using an accelerator type neutron source.

2. Description of the Related Art

Neutron porosity well logging instruments are used primarily to determine the volumetric concentration of hydrogen nuclei within earth formations. The volumetric concentration of hydrogen nuclei is a parameter of interest because it is generally related to the fractional volume of pore space (referred to as the "porosity") of the earth formations. Fluids typically present in the pore spaces of earth formations include water and/or some mixtures of petroleum compounds. Water and petroleum compounds include chemically combined hydrogen. Indications of high volumetric concentrations of hydrogen, therefore, typically correspond to high fractional volumes of fluid-filled pore space ("porosity"). High porosity typically corresponds to earth formations which are capable of producing commercial quantities of materials such as petroleum.

Neutron porosity well logging instruments known in the art include so-called "compensated" thermal neutron instruments. Compensated thermal neutron instruments generally have two or more detectors sensitive to thermal neutrons. The detectors are positioned at spaced apart locations from a source of high energy neutrons. The neutron source is typically a so-called "steady-state" or "chemical" source which emits substantially continuous numbers of high-energy neutrons. Steady-state neutron sources used for thermal neutron porosity well logging include radioisotopes such as americium-241 disposed inside a beryllium "blanket". The neutrons emanating from this type of steady-state source have an average energy of about 4.5 million electron volts (MeV). The detectors can include helium-3 gas ionization tubes (also called helium proportional counters) which are particularly sensitive to neutrons at the thermal energy level, generally considered to be a most probable energy of about 0.025 electron volts (eV).

In determining porosity using a compensated thermal neutron instrument, the high energy neutrons emitted from the steady-state source travel into the earth formations where they gradually lose energy, primarily by collision with hydrogen nuclei within the earth formations. As the neutrons are reduced in energy to the thermal level they can be detected by either of the detectors. Compensated thermal neutron instruments are typically configured so that the numbers of neutrons detected by each of the detectors (the "count rate" at each detector) are scaled into a ratio of count rates. The ratio is typically the count rate of the detector closer to the source (the "near" detector) with respect to the count rate of the more spaced apart ("far") detector. The count rate ratio can be further scaled, by methods well known in the art, into a measurement corresponding to formation porosity. The pore spaces are assumed to be filled with fresh water in scaling the ratio into porosity. Alternatively, the ratio can be scaled into volumetric hydrogen concentration (the so-called "hydrogen index"). Scaled ratio measurements are typically referred to for the sake of convenience as the "neutron porosity" of the earth formations, and more specifically are referred to as the "thermal neutron porosity" when made with a compensated thermal neutron instrument.

A particular drawback to the compensated thermal neutron instruments known in the art is that they use steady-state neutron sources. Steady-state neutron sources emit neutrons at all times and expose the system operator to some neutron radiation until the instrument is lowered into the wellbore. For safety reasons it would be preferable to have a thermal neutron porosity instrument which is substantially non-radioactive until it is inserted into the wellbore.

Another drawback to steady-state neutron sources is that they have relatively low neutron output, at least in part intentionally so that the instrument may be used relatively safely by the system operator. The statistical precision of thermal neutron porosity logs could be improved if the neutron output could be increased, but the strength of the steady state source is generally limited by such safety considerations.

A neutron source known in the art as an "accelerator" neutron source, such as one described in U.S. Pat. No. 4,996,017 issued to Ethridge, is only very slightly radioactive until appropriate control voltages are applied to the accelerator. Sources such as the one described in the Ethridge '017 patent are used in a number of different types of neutron instruments, most commonly instruments which measure properties of the earth formations such as the thermal neutron capture cross-section. Accelerator sources typically emit neutrons in discrete, short-duration "bursts" corresponding to application of the appropriate control voltages to the accelerator. The bursts comprise neutrons having an average energy of about 14 MeV. The relatively high energy of the neutrons emanating from the accelerator source, when compared with the neutrons emanating from the steady-state source, however, makes determination of thermal neutron porosity difficult when an accelerator source is used.

Using accelerator sources for measurement of "epithermal" neutron porosity and for other neutron interactive properties, such as the capture cross-section of earth formations, is well known in the art. For example, U.S. Pat. No. 4,152,590 issued to Schultz et al describes a pulsed-neutron instrument which simultaneously measures thermal neutron capture cross-section and apparent "epithermal" neutron porosity of the earth formations. The porosity measurements made by the instrument disclosed in the Schultz et al '590 patent is referred to as "epithermal" neutron porosity because this instrument detects neutrons primarily at the epithermal energy level (defined as greater than approximately 1 eV average energy). While measurements of epithermal neutron porosity are useful, they do not correspond exactly to neutron porosity measurements made from detections of thermal neutrons, particularly due to such environmental factors as salinity of water in the wellbore or in the pore spaces of the formation, and the possible presence of thermal neutron absorptive materials such as boron in the wellbore or earth formation. Therefore the instrument disclosed in the Schultz et al '590 patent does not provide measurements which can directly substitute for those made by thermal neutron porosity measuring instruments which use steady-state sources.

Other accelerator source neutron instruments known in the art include detectors which are sensitive to gamma ray photons emitted by nuclei in the earth formation as a result of "capture" of thermal neutrons. These instruments are primarily intended to make measurements corresponding to the thermal neutron capture cross-section ("sigma") of the earth formations, rather than the thermal neutron porosity. Measurements made by these instruments are not highly correspondent to thermal neutron porosity.

Still other accelerator source neutron porosity instruments are described in U.S. Pat. No. 5,399,184 issued to Wraight and U.S. Pat. No. 5,051,581 issued to Hertzog et al. The instruments described in these patents are primarily intended to measure epithermal neutron porosity, which as previously explained, does not correspond to thermal neutron porosity because of certain environmental factors.

It has been proposed to adapt accelerator-type neutron sources directly to instruments configured as are those which steady state neutron source. Mere adaptation of an accelerator-type neutron source for use in a compensated thermal neutron porosity instrument, without more however, has not yielded good results in determining thermal neutron porosity. FIG. 1, for example, shows at curve 102, a graph of the detector count rate ratio with respect to water-filled fractional pore volume (porosity) for a typical compensated thermal neutron device using a steady-state source known in the art. As can be observed in curve 102, even for very high fractional pore volumes (porosities), there is still a discernible correspondence between the ratio and the porosity. Direct replacement of the steady-state source with an accelerator-type source in the thermal neutron device known in the art yields a response as shown in curve 104. As can be observed in curve 104, at porosities above about 20 percent, a thermal neutron instrument designed only according to specifications known in the art for steady-state source instruments but using an accelerator type source, has substantially no porosity sensitivity. The relatively poor porosity sensitivity in the simulated accelerator source thermal neutron instrument whose response is shown by curve 104 is primarily related to the different "slowing down" length of the 14 MeV neutrons emanating from the accelerator source compared to the slowing down length of the 4.5 MeV neutrons from the steady-state source. It is generally believed by those skilled in the art that higher initial neutron energy results in relatively poorer porosity sensitivity.

One adaptation of an accelerator type neutron source to neutron well logging is described in U.S. Pat No. 3,818,225 issued to Smith. The apparatus described in the Smith '225 patent includes an accelerator type neutron source and two axially spaced apart neutron detectors. A radiation "shield" is interposed between the source and the nearer of the two detectors ("near" detector) to reduce the number of neutrons which are transmitted directly along the instrument and which did not interact with the earth formations adjacent to the instrument. The Smith '225 patent suggests using iron, lead or other suitable material for the shield. The Smith '225 patent further states that the shield is not a necessary component of the apparatus. As can be seen in the graph of FIG. 1, an instrument having an accelerator source and detectors arranged according to the Smith '225 patent without using any shield in between the source and the detectors will have poor porosity sensitivity. The apparatus in the Smith '225 patent includes a feature intended to overcome the poor porosity sensitivity obtained when using accelerator neutron sources for thermal neutron porosity measurement. This feature is a "gating" mechanism which counts only the thermal neutron population at each of the two detectors during two discrete, short time intervals following the burst of high energy neutrons. The purpose of measuring neutrons only during these discrete time intervals is to measure neutrons which have traveled a greater distance from the source and which are more indicative of the properties of the earth formations such as porosity. A drawback to "gating" the neutron counts as described in the Smith '225 patent is that the short measurement intervals reduce the total numbers of neutrons actually counted for porosity calculation so as to make the statistical precision of the instrument unacceptable at commercially useful logging speeds (the "logging speed" being the rate at which the instrument moves through the wellbore). The reason that the material used for the "shield" is not important to the operation of the apparatus disclosed in the Smith '225 patent is that discrimination of neutron energy to improve porosity resolution is accomplished by "gating" the neutrons counted. Yet another drawback to time-discrimination of neutron counting is that counting only the limited number of neutrons in the "gates" as contemplated by Smith '225 may result in the porosity measurement being overly sensitive to the neutron capture cross-section of the earth formation.

Another drawback to the apparatus in the Smith '225 patent is the type of "shield" material suggested. Iron, in particular, has a high enough neutron capture cross-section to make the statistical precision of the resulting neutron porosity data be unacceptable at commercial logging speeds even if the neutron counts are not "gated". While the other "shield" material disclosed in Smith '225, namely lead, does not have as large a neutron capture cross-section as iron, using lead as a shield, without more, will not provide the instrument with acceptable porosity resolution.

U.S. Pat. No. 3,842,264 issued to Arnold describes a pulsed neutron logging instrument having a neutron radiation shield interposed between the source and the nearer of two axially spaced apart detectors. Arnold '264 describes the shield as consisting of cadmium, paraffin, iron, copper or the like. The shielding materials described by Arnold '264 are generally intended to prevent passage of neutrons directly along the instrument, and so can include materials such as cadmium which have a very high neutron capture cross section. The apparatus in the Arnold '264 patent, however, includes detectors which are sensitive to capture gamma rays, because the instrument in the Arnold patent is adapted to measure the neutron capture cross section of earth formations, rather than the thermal neutron porosity. Some of the materials suggested for use in the Arnold patent for the shield, particularly paraffin and cadmium, tend to disturb the spatial distribution of thermal neutrons in the earth formation so as to make determining thermal neutron porosity difficult. The materials suggested by Arnold also tend to have either a short neutron "slowing-down" length (paraffin), or a capture cross-section which is unacceptably high (copper, iron, cadmium) to provide acceptable porosity sensitivity and statistical precision for a commercially acceptable thermal neutron porosity instrument.

U.S. Pat. No. 4,570,067 issued to Gadeken describes a combination thermal/epithermal neutron porosity instrument. The instrument in the Gadeken '067 patent includes a source of high energy neutrons and a pair of special neutron detectors. The source is described as either a chemical source or a pulsed neutron source. The Gadeken apparatus further includes a shielding material interposed between the source. The shielding material is described as one having the property of effectively "slowing down" the fast neutrons emanating from the source, such as any highly hydrogenous material. While this arrangement may be suitable for use with a chemical ("steady-state") source, it has been determined that using a shield material with a short neutron "slowing-down" length, as would be any highly hydrogenous material, is unsuitable for use with a pulsed-source thermal neutron porosity instrument because of the unfavorable effects on statistical precision and porosity sensitivity. The principal effect of using a shield material having a short neutron slowing down length between the source and the nearer detector is to disturb the spatial distribution of thermal neutrons, which makes determining the thermal neutron porosity difficult.

Still another accelerator type neutron instrument is described in U.S. Pat. No. 3,621,255 issued to Schwartz. This instrument includes two neutron detectors in a "nested" arrangement spaced apart from an accelerator type neutron source. A "shield" material is interposed between the source and the near detector. The shield material is described as a neutron "moderating" material or a neutron "absorbing" material or an appropriate combination of these substances, such as graphite combined with boron. Neutrons counts from each of the detectors in the instrument in the Schwartz '255 patent are segregated with respect to the time from the end of the neutron "burst". The neutron counts which are used to determine porosity are described as those detected during time period in which the counts decrease with respect to time after the neutron burst (the "decay" period). It has been determined that limiting the neutron counts for porosity determination to those detected during the decay period results in unacceptable porosity sensitivity and statistical accuracy. It has also been determined that the shield material suggested in the Schwartz '255 patent, namely a combination of graphite and boron, provides unacceptable porosity sensitivity and statistical precision, even using boron concentrations as low as 1 percent for a shield as described in the Schwartz '255 patent. Other materials which are known in the art to be neutron "moderators" such as water or plastic have been tested by numerical simulation for an instrument configured as the one shown in the Schwartz '255 patent. As a result of the simulation experiments such materials are expected to have unacceptable porosity sensitivity and statistical accuracy.

SUMMARY OF THE INVENTION

The invention is an apparatus for measuring the thermal neutron porosity of earth formations penetrated by a wellbore. The apparatus includes an elongated housing adapted to traverse the wellbore, a selectively controllable source of high-energy neutrons, a near detector primarily sensitive to thermal neutrons and axially spaced apart from the source, a far detector also primarily sensitive to thermal neutrons and axially spaced apart from the source so that the near detector is axially disposed between the source and the far detector. The apparatus includes a neutron shield disposed between the near detector and the far detector, and a neutron scattering insert inside the housing between the source and the near detector. The neutron scattering insert consists of a material selected from the group of aluminum, silicon, graphite, beryllium, sulfur, potassium, lead and magnesium. In a preferred embodiment of the invention, the scattering insert consists of aluminum. The neutron shield consists of a material which moderates and absorbs neutrons, such as boron-10 doped plastic.

Another embodiment of the invention includes at least one epithermal neutron detector. The second embodiment of the invention includes a computer for calculating the epithermal neutron porosity of the earth formation from the numbers of epithermal neutrons detected by the epithermal neutron detector.

In a method of determining thermal neutron porosity of an earth formation according to the invention, the formation is irradiated with bursts of high energy neutrons. The neutrons are detected at axially spaced apart locations from the neutron source. The neutrons are scattered at a location axially between the source and the nearmost one of the detectors. The scattering is performed by a material selected from the group of aluminum, silicon, graphite, beryllium, sulfur, potassium, lead and magnesium. The neutrons are shielded from travelling axially between the spaced apart locations at which the neutrons are detected by a material which moderates and absorbs neutrons, such as boron-10 doped plastic. The porosity is determined from the ratio of neutrons-counted at the nearmost location with respect to the neutrons counted at the more distant location

DESCRIPTION OF THE PREFERRED EMBODIMENT

Figure 2:
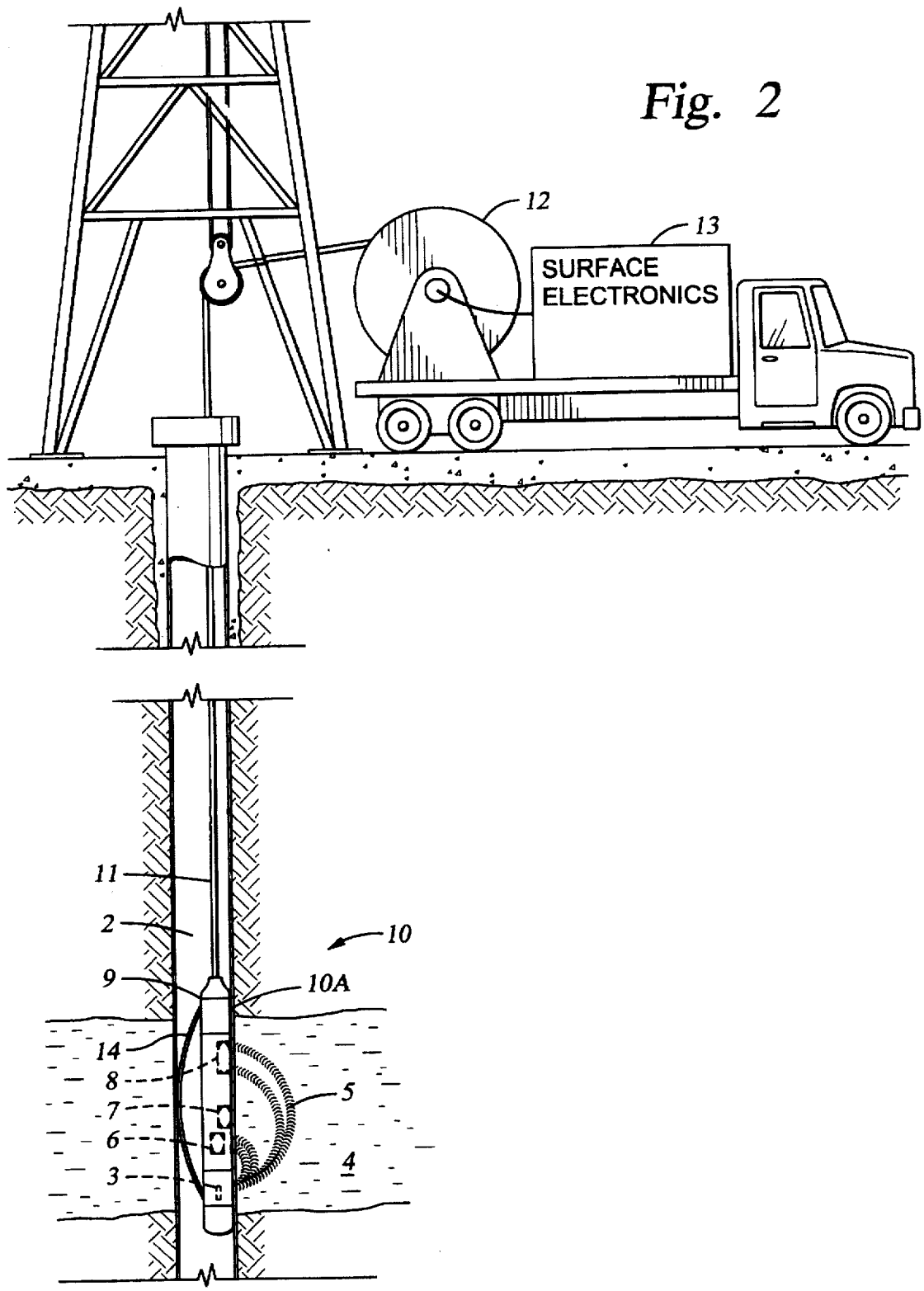
FIG. 2 shows the apparatus of the invention as it is used in a wellbore.

1. Configuration of a Neutron Porosity Logging Instrument According to the Invention FIG. 2 shows a neutron porosity well logging instrument 10 according to the invention as it is typically used in a wellbore 2 penetrating earth formations 4. The neutron porosity instrument 10 can be lowered into the wellbore 2 at one end of an armored electrical cable 11. The cable 11 can be extended into and withdrawn from the wellbore 2 by means of a winch 12 or similar spooling device known in the art. The surface end of the cable 11 can be electrically connected to a surface electronics system 13 which can include recording systems (not shown separately) for generating a record, with respect to depth in the wellbore 2, of measurements made by the neutron porosity instrument 10 which are transmitted along the cable 11. The recording systems can also include any form of computer (not shown) which can calculate values of neutron porosity of the formations 4 from the measurements made by the instrument 10.

The neutron porosity instrument 10 includes a source 3 of high-energy, or "fast", neutrons. In the present embodiment the source 3 can be a controllable accelerator-type such as one described, for example, in U.S. Pat. No. 4,996,017 issued to Ethridge. The source 3 is typically disposed within a sealed, elongated housing 10A adapted to traverse the wellbore 2. Also disposed inside the housing 10A are a near detector 6, a neutron shield 7 and a far detector 8. The detectors 6, 8 should be primarily sensitive to thermal neutrons, as will be further explained. An eccentralizing device, shown at 14, is typically attached to the housing 10A to push one side of the housing 10A into contact with the wall of the wellbore 2. The eccentralizing device 14 can be a bowspring or other type of eccentralizing device known in the art.

The source 3 periodically emits short-duration pulses, or "bursts" of high-energy neutrons, shown generally at 5. When they are first emitted from the source 3, the neutrons 5 have an average energy of about 14 million electron volts (MeV). Some of the high energy neutrons 5 enter the earth formations 4 and can interact in various ways with the atomic nuclei in the formations 4. The neutrons 5, among other things, are caused to slow down by collision with the atomic nuclei within the formations 4. Some of the neutrons 5 can be deflected upon certain collisions in a direction back towards one of the detectors 6, 8 where they may be detected. Each detector 6, 8 is electrically connected to a telemetry/controller unit 9 which can impart signals to the cable 11 corresponding to the detections of neutrons at each one of the detectors 6, 8. These signals can be decoded in the surface electronics system 13 in order to determine the numbers (the "counts") of neutrons detected by each of the detectors 6, 8. Alternatively, the signals can correspond to a ratio of counts of each of the detectors 6, 8. As is well known in the art, the ratio can correspond to porosity of the formations 4. The computer (not shown) can be programmed to calculate porosity from, among other measures, the ratio of counts. It is also contemplated that the telemetry/controller unit 9 can include a recording device (not shown) to store the count and/or ratio signals for later processing. It is not necessary, although it is convenient to the operation of the invention, to transmit the count and/or ratio signals to the surface electronics system 13 while the instrument 10 is disposed in the wellbore 2.

Generally, the highest statistical precision will be obtained when the instrument 10 is configured to count substantially all the neutrons detected by both the near 6 and far 8 detectors. Prior art neutron instruments, such as one disclosed in U.S. Pat. No. 3,818,225 issued to Smith, for example, used "gating" or similar "time from the burst"-based temporal discrimination as to which detected neutrons were actually counted for purposes of porosity determination. Time-based discrimination with the intent of improving porosity resolution has generally reduced the statistical precision so as to make the useful logging speed of such instruments tool low to be commercially acceptable. The instrument 10 of the invention, therefore, does not use any form of temporal discrimination in detected neutron counting.

Figure 3:
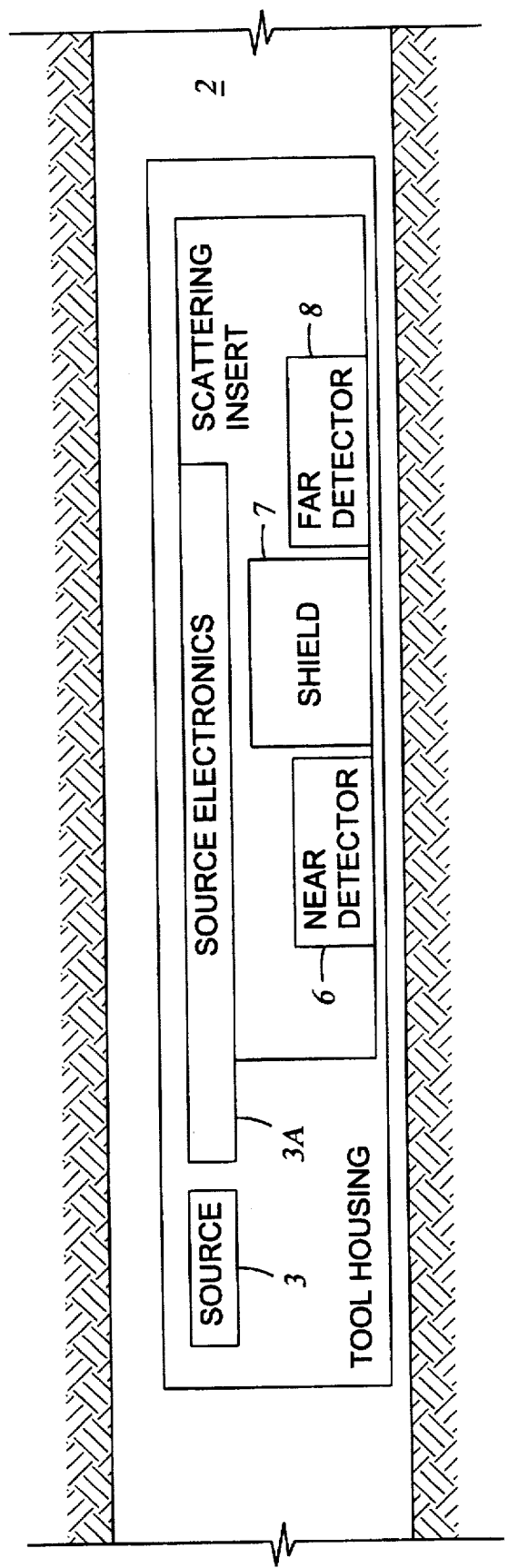
FIG. 3 shows a cross-sectional view of the apparatus of the invention.

The design of the instrument 10 itself can be better understood by referring to FIG. 3. The source 3 can be disposed near one end of the housing 10A. The source 3 can be operated at a frequency of about 5–10 KHz in order to accommodate the inclusion of epithermal neutron detectors (not shown in FIG. 3) in the instrument 10 for purposes which will be further explained. The neutron bursts emanating from the source 3 typically have a duration of about 20–40 microseconds each. As shown in FIG. 3, the source 3 can be radially offset towards the side of the housing 10A opposite to the side which is pressed up against the wall of the wellbore 2. Radially offsetting the source 3 is a only matter of convenience for the system designer in order to be able to fit the source 3 and associated electronic circuits 3A in proper axial relationship to the detectors 6, 8. The radial position of the source 3 within the housing 10A is not to be construed as a limitation on the invention.

The near detector 6 can be a 1 inch diameter, 3 inch long helium proportional counter having a gas pressure of about 10 atmospheres. The center of the near detector 6 is preferably positioned about 11 inches from the "target" in the source 3. The near detector 6 is preferably positioned so that it is radially displaced towards the wall of the housing 10A which is urged into contact with the wellbore 2 by means of the bowspring (14 in FIG. 2). The radial position of the near detector 6, however, is a matter of convenience for the system designer and is not to be construed as a limitation on the invention.

The far detector 8 can be a 2 inch diameter, 8 inch long helium proportional counter having a gas pressure of about 10 atmospheres. The center of the far detector 8 is preferably positioned about 21 inches from the source 3 "target". The far detector 8 can also be radially displaced towards the wall of the housing 10A which is urged into contact with wall of the wellbore 2. The radial position of the far detector 8 is also a matter of convenience for the system designer and is not to be construed as a limitation on the invention.

It is also to be understood that the selection of helium proportional counters for the detectors 6, 8 is a matter of convenience for the system designer and is not to be construed as a limitation on the invention. Other types of thermal neutron detectors could be used in the invention which would provide acceptable results. For example, lithium-6-doped glass scintillation counters could be substituted for the helium proportional counters used in this embodiment of the invention.

The neutron shield 7 is axially positioned in between the near detector 6 and the far detector 8. The shield 7 reduces the number of neutrons travelling along the interior of the housing 10A between the near detector 6 and the far detector 8. The shield 7 is preferably made from material which both reduces the energy level of neutrons (acts as a neutron "moderator") and can absorb thermal neutrons. The shield 7 preferably can be composed of a boron-10 doped plastic. Boron-10 doped plastic performs both the functions of neutron moderator and thermal neutron absorber, which combination makes an effective neutron shield for purposes of the invention. Such compositions of boron-10 doped plastic used for the shield 7 are known in the art. Alternatively, the shield 7 can include a first layer of titanium hydride as the moderator and a second layer of metallic cadmium as the thermal neutron absorber. Other combinations of materials for performing the neutron moderating and the neutron absorbing functions are known in the art and may be successfully substituted for the material used in the shield 7.

A neutron scattering insert 15 is positioned axially between the source 3 and the near detector 6. The scattering insert 15 can fill substantially the entire volume of the housing 10A between the source 3 and the near detector 6. The scattering insert 15 optionally can fill a substantial portion of the volume of the interior of the housing 10A which is not occupied by the detectors 6, 8 and the shield 7, and which extends axially between the near detector 6 and the far detector 8. The extension of the scattering insert 15 axially past the near detector 6, the shield 7 and the far detector 8 is a matter of convenience for the system designer, which in the present embodiment provides a rigid mounting facility for the electronic circuits 3A associated with the source 3. It is to be understood that the intended function of the scattering insert 15, which will be further explained, is provided substantially entirely by that portion of the insert 15 which is axially disposed between the source 3 and the near detector 6. The insert 15 could therefore be formed without the axial extension past the shield 7 and the far detector 8. The neutron scattering insert 15 may include a recess as shown in FIG. 3 to accommodate the source electronic circuits 3A, but this is a matter of convenience for the system designer and is not an essential feature of the scattering insert 15.

2. Selection of a Suitable Material for the Scattering Insert

The purpose of the scattering insert 15 is to reduce the number of neutrons which directly enter the near detector 6 and the far detector 8 from the source 3, with as little disturbance as is practical to the energy distribution of neutrons in the earth formations. The scattering insert 15 in this embodiment can be made from aluminum, but the important properties of the material from which the scattering insert 15 is made are generally that it have a high ratio of neutron scattering cross-section with respect to its neutron capture cross-section. The material preferably includes a relatively high atomic number (Z) consistent with a high ratio. It should be noted that these properties are substantially opposite of the neutron interaction properties of the shield 7, which should have a high neutron capture cross-section and a low neutron scattering cross-section. It is contemplated that other materials, for example beryllium, graphite, lead, silicon, magnesium, potassium and sulfur which generally have a high ratio of neutron scattering cross-section to neutron capture cross-section will also perform satisfactorily for use as the scattering insert 15. The usefulness of these materials has been verified by numerical simulation as will be further explained.

Of these materials, aluminum has the particular advantages of low density, high strength and is easily machined, but as previously explained, the use of aluminum is not meant to be an exclusive representation of materials which can perform the required function of the scattering insert 15.

It has been determined that positioning of the neutron scattering insert 15 substantially as shown in FIG. 3, and selecting a material such as one described herein for the scattering insert 15, will provide the logging instrument with commercially useful porosity sensitivity. Using the scattering insert 15 as described herein, therefore, makes possible a useful thermal neutron porosity instrument using an accelerator type source 3. Prior art thermal neutron porosity instruments, which more often use steady-state neutron sources, typically include a neutron moderating/absorbing "shield" (which can be similar in design and composition to the shield 7 of the invention) axially disposed between the near detector and the source. See for example, U.S. Pat. No. 3,621,255 issued to Schwartz or U.S. Pat. No. 4,005,290 issued to Allen. It has been determined by numerical simulation of response that placement of a shield according to the prior art, in combination with an accelerator-type source as used in the invention, would not provide the resulting thermal neutron porosity instrument with commercially acceptable porosity sensitivity.

3. Numerical Simulation Results

Figure 1:
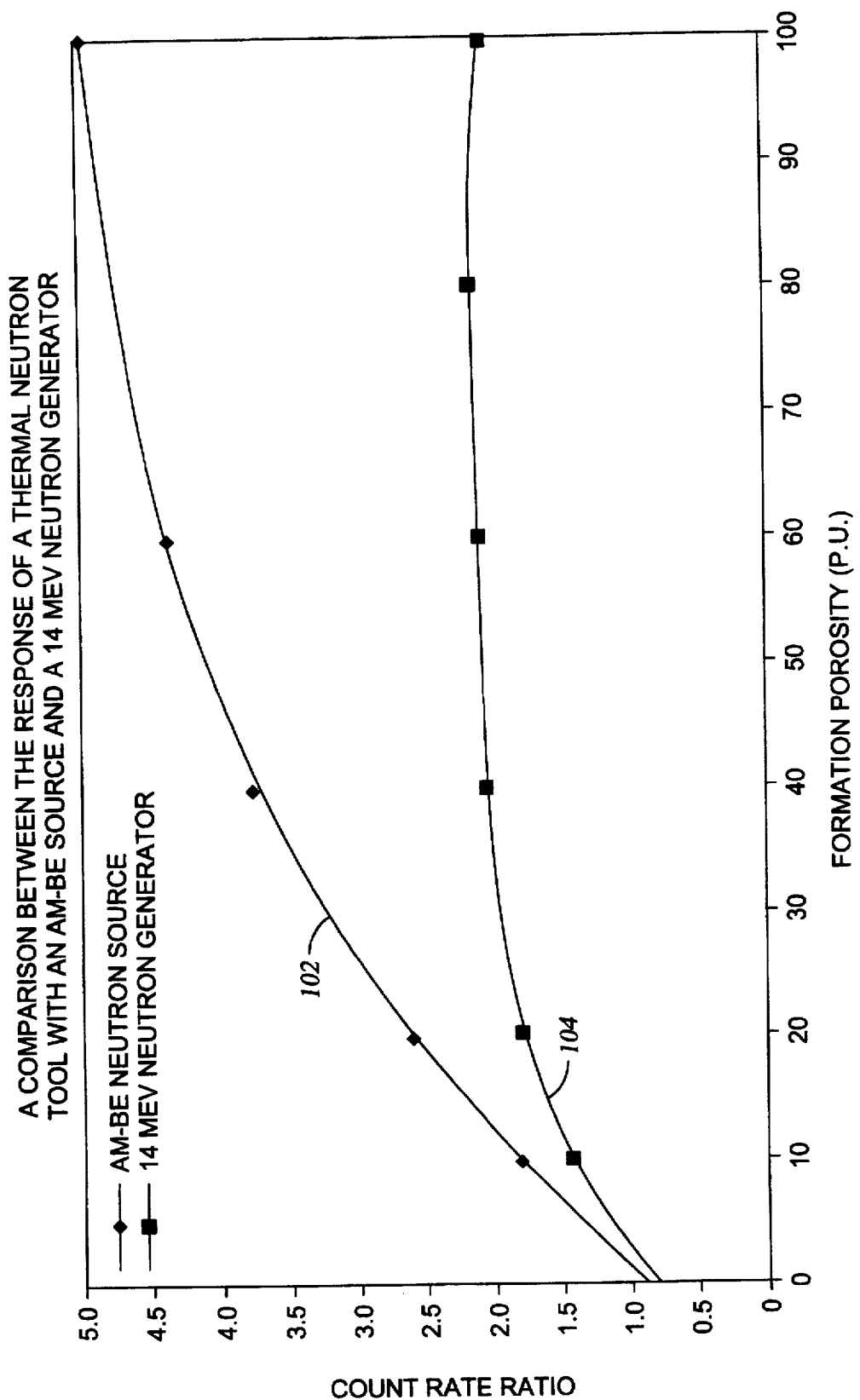
FIG. 1 shows porosity sensitivity of prior art thermal neutron devices using a steady-state neutron source compared with porosity sensitivity of such as device using an accelerator type neutron source.
Figure 4:
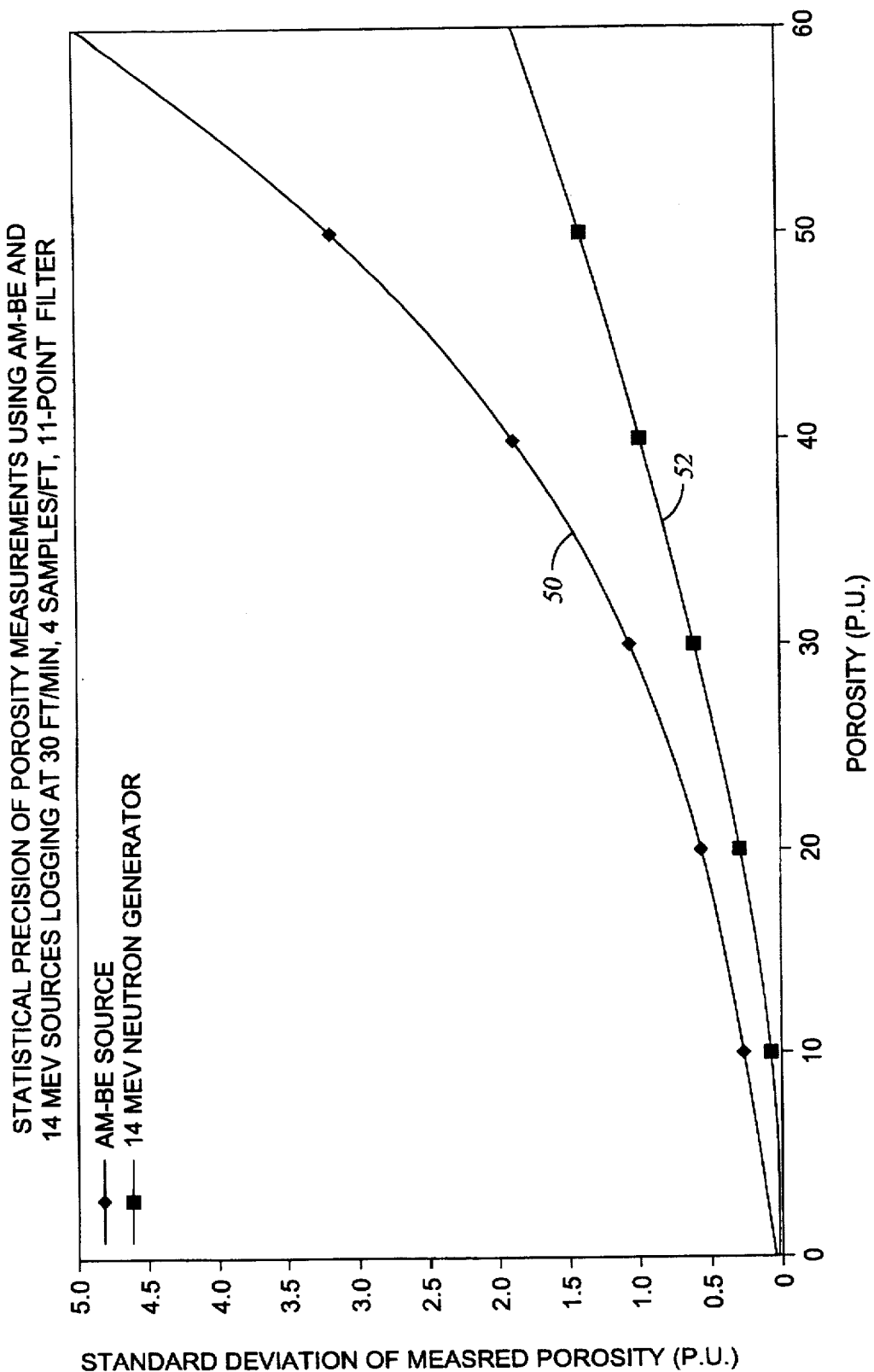
FIG. 4 shows a graph of the expected statistical precision of the invention compared with prior art instruments.

The response of an instrument configured as described herein and shown in FIG. 3 was simulated using Monte Carlo modelling. Monte Carlo modelling is known in the art for simulating the response of nuclear particle interactions. FIG. 4 shows a graph of the statistical precision of the instrument (10 in FIG. 1) of the invention compared with the statistical precision of prior art compensated thermal neutron porosity devices using a steady-state neutron source. The simulation was performed so that the instruments, both the invention and the prior art types, are assumed to move through the simulated wellbore (2 in FIG. 2) at a rate of 30 feet per minute. Ratios, and corresponding porosity values, were computed at a rate of four per linear foot of the simulated wellbore traversed by the instruments. The statistical precision was calculated at 0, 10, 20, 40 and 60 percent fractional pore volume (referred to as "porosity units" or p. u.) and best fit curves were calculated for each set of points. Curve 50 represents the statistical precision of prior art thermal neutron instruments. The statistical precision of the instrument of the invention can be observed at curve 52. Even at fractional pore volumes of 30 percent (30 p. u.) the instrument according to the invention has statistical precision within about 1 p. u., which represents an improvement over the prior art.

Figure 5:
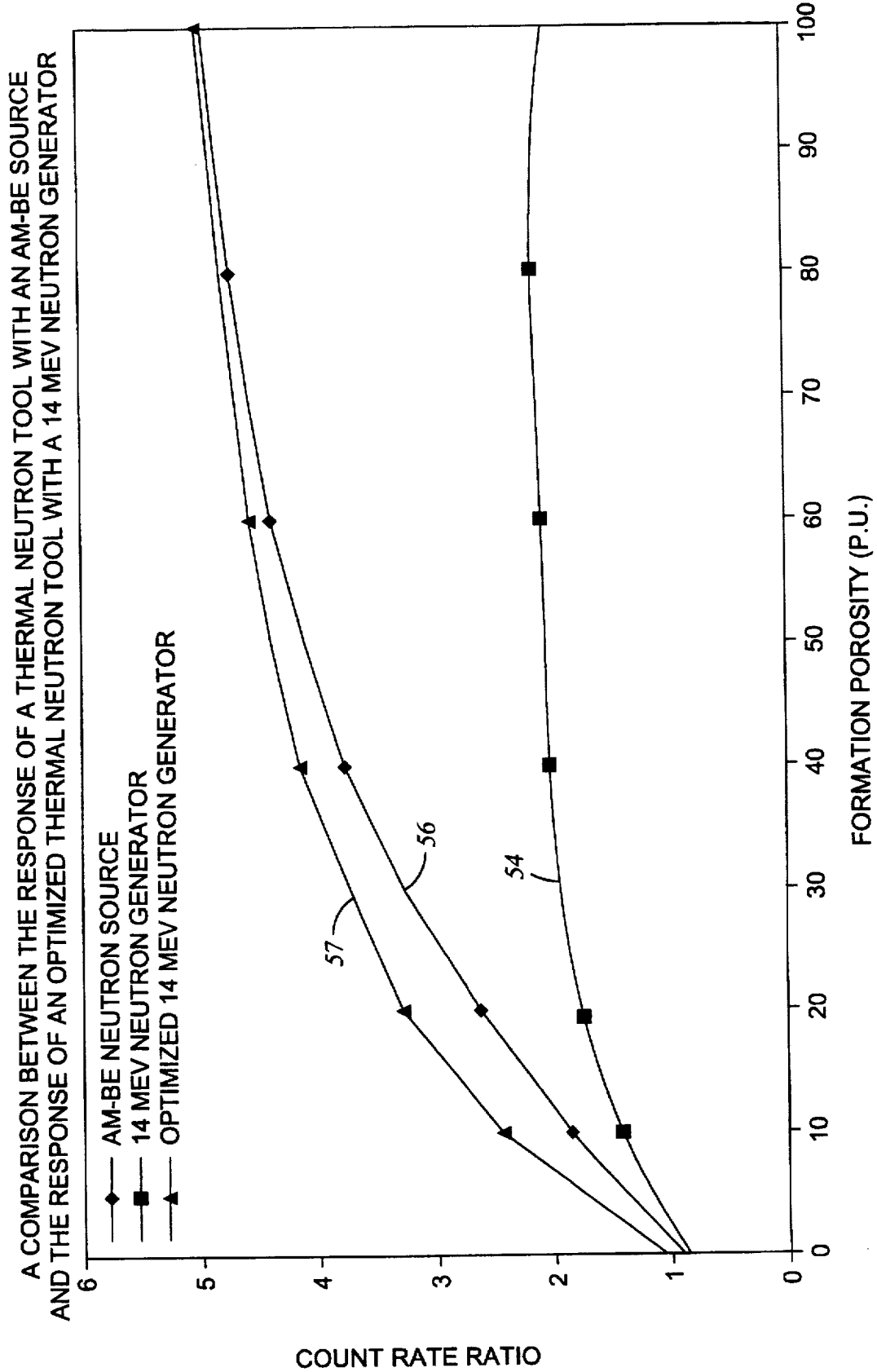
FIG. 5 shows a graph of the porosity sensitivity of the invention compared with prior art instruments.

FIG. 5 shows a graph indicating the expected porosity sensitivity of the invention. For purposes of comparison with the invention, the graph in FIG. 5 includes curves (shown previously as 102 and 104 in FIG. 1) representing the relationship of count rate ratio with respect to porosity for, respectively, the thermal neutron device of the prior art using a steady-state source (shown at 102 in FIG. 1) at curve 56, and a direct adaptation of the accelerator source to the prior art thermal neutron device at curve 54 (shown in FIG. 1 at 104). As can be observed in FIG. 5 at curve 57, the invention provides a sensitive relationship between count rate ratio and porosity.

Figure 6:
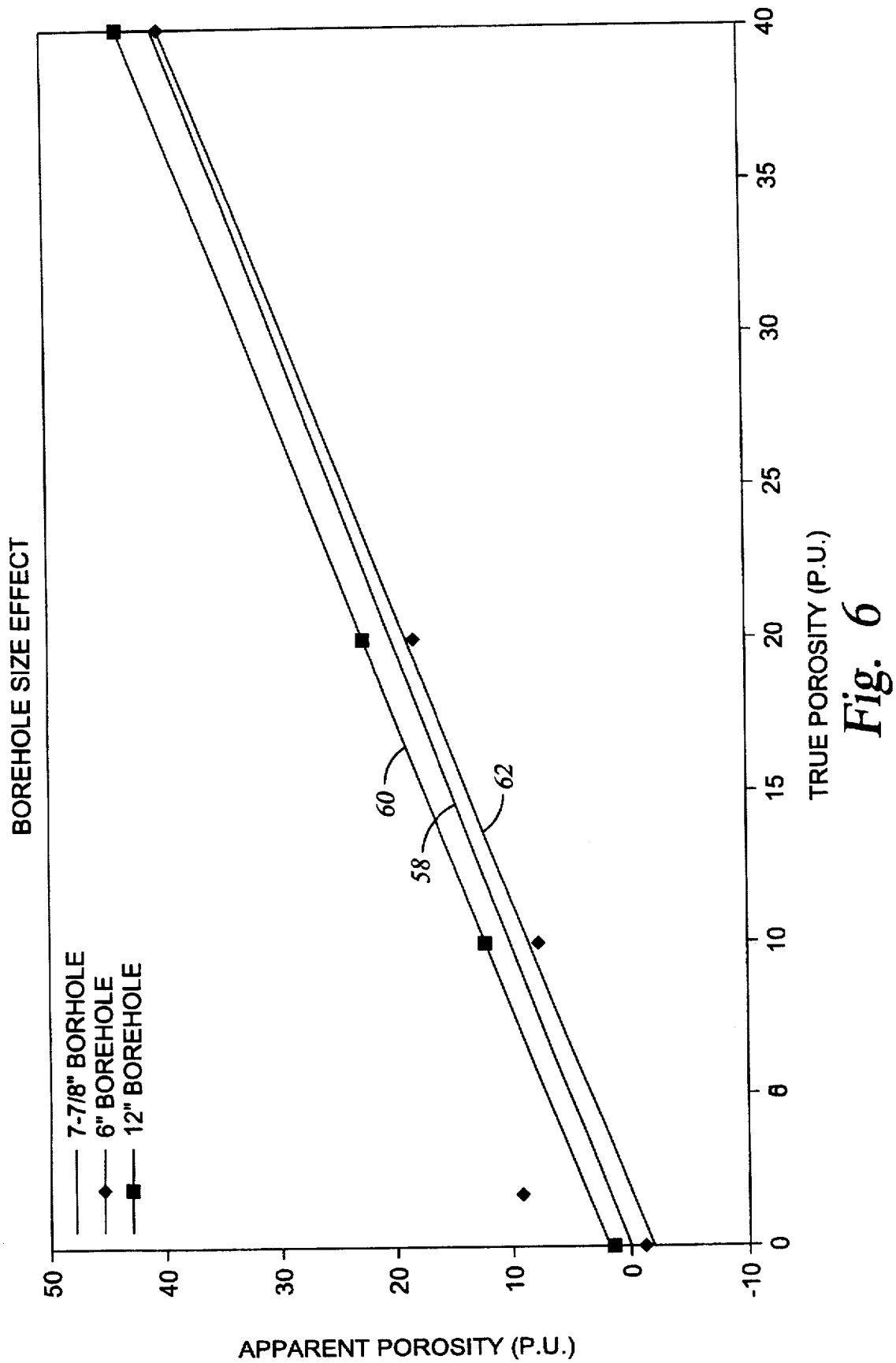
FIG. 6 shows a graph of effects of diameter of the wellbore on the response of the invention.

FIG. 6 shows a graph of the expected effect of the size of the wellbore (2 in FIG. 2) on the measurement of porosity made by the invention. The relationship between count rate ratio and porosity, for most thermal neutron devices, is scaled to the response of the instrument in a fresh water filled wellbore having a diameter of 7.875 inches. In FIG. 6, this is represented at curve 58, where there is a substantially perfect relationship between apparent porosity and true porosity. The response of the invention to fresh water filled wellbore having a diameter of 12 inches is shown at curve 60. The response of the invention to a 6 inch fresh water filled wellbore is shown at curve 62. Even at porosities of 40 p. u., the invention exhibits only about 3 p. u. variation in apparent measurement when operating in a 12 inch wellbore.

Figure 7:
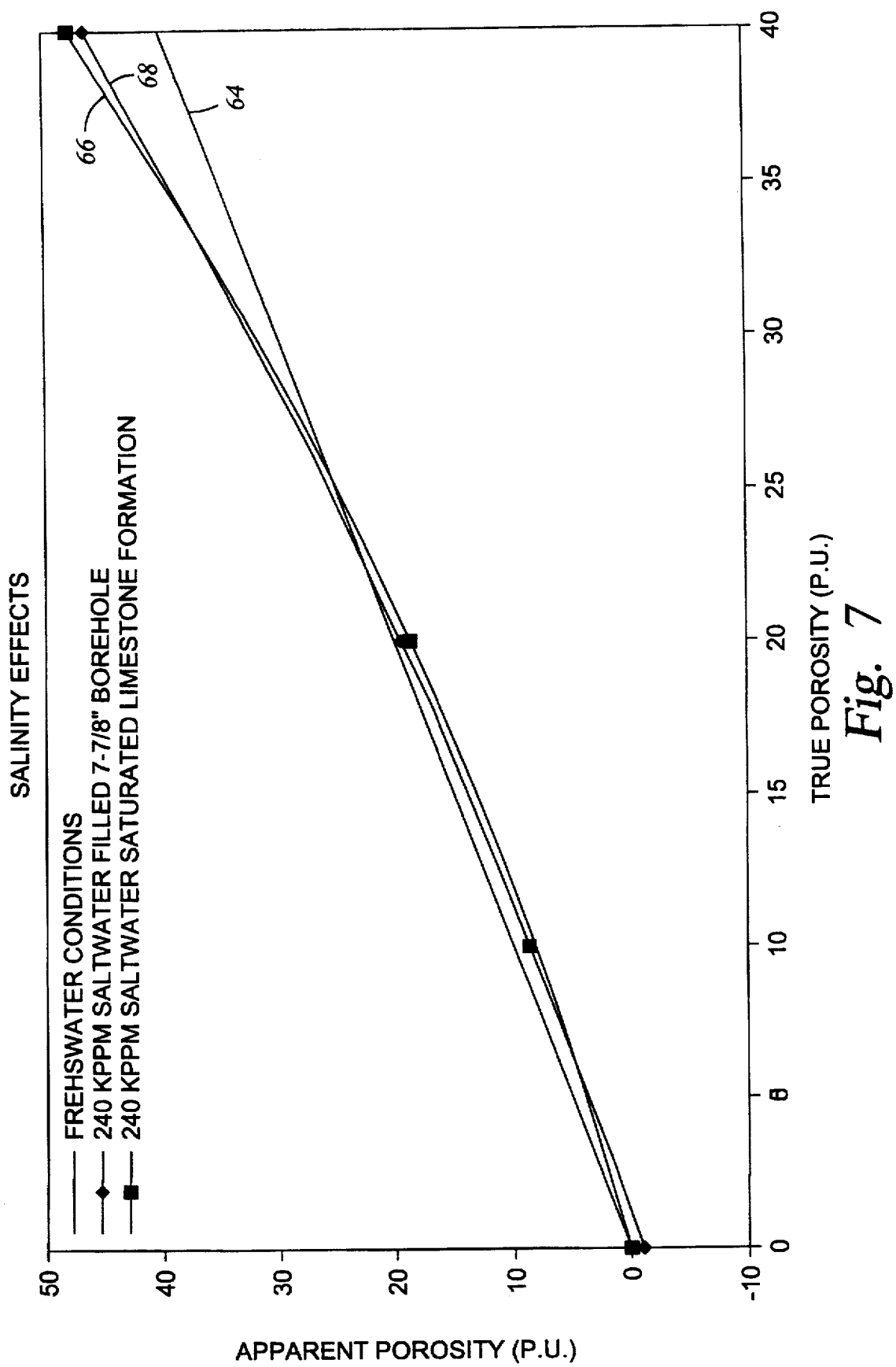
FIG. 7 shows a graph of the effects of salinity on the response of the invention.

FIG. 7 shows a graph of the expected effect of salinity of the fluid in the pores spaces of the earth formation (4 in FIG. 2). The response of the invention to fresh water is shown at curve 64. The response of the invention to substantially salt-saturated (240,000 ppm concentration of sodium chloride) fluid in the pore spaces of limestone formations is shown at curves 68 for a fresh water filled wellbore, and at curve 66 when the wellbore is itself filled with salt-saturated fluid. The salinity effect on the response of the invention is negligible at porosities below about 27 p. u. As is understood by those skilled in the art, the salinity effect, as well as the hole size (wellbore diameter) effect described previously and shown in the graphs of FIG. 6, can be substantially corrected during operation of the instrument (10 in FIG. 2) by programming the surface electronics (13 in FIG. 2) to make appropriate adjustments to the apparent measurement of porosity.

Figure 8:
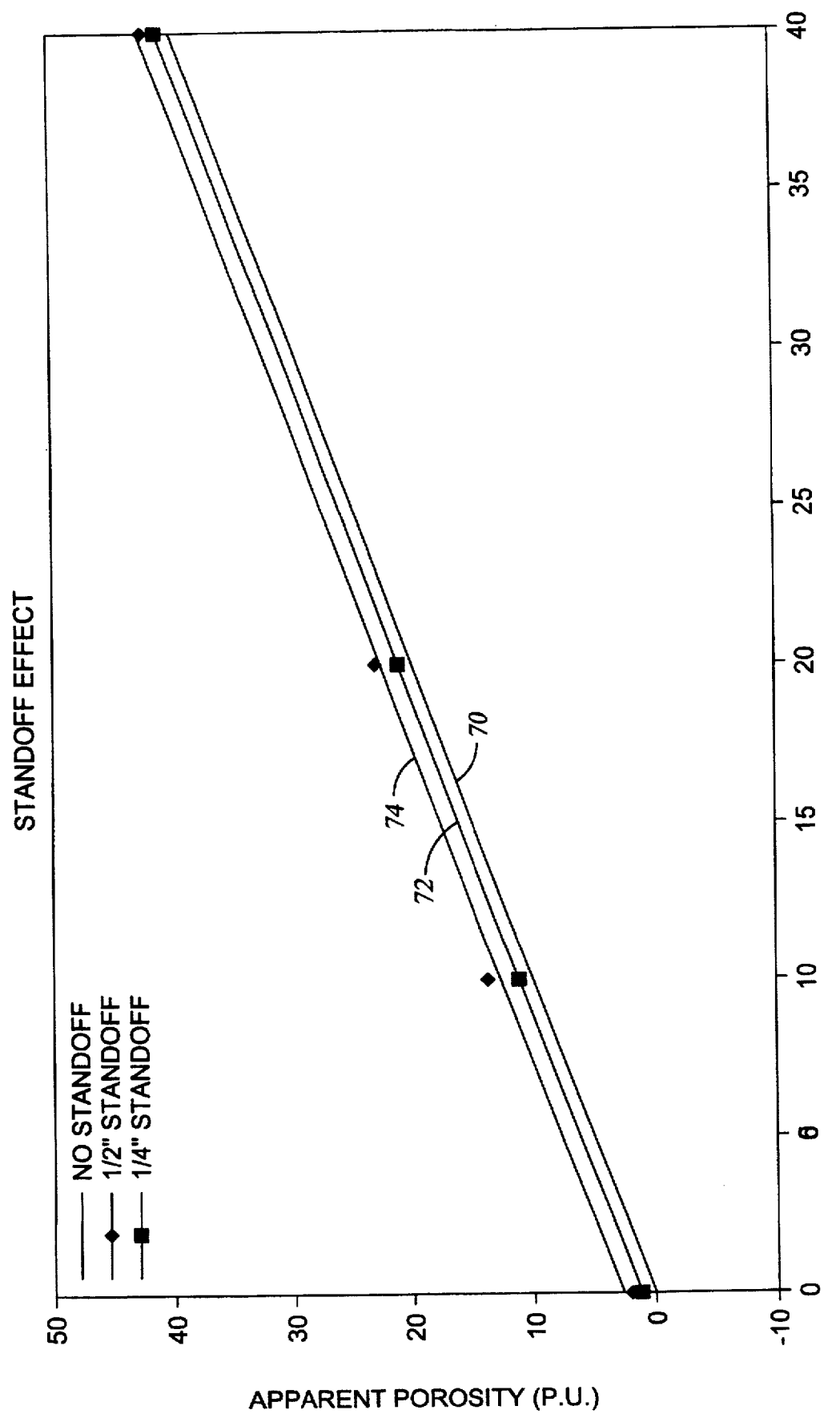
FIG. 8 shows a graph of the effect of tool standoff from the wall of the wellbore for the invention.

FIG. 8 shows a graph of the expected effect on the response of the instrument when the housing (10A in FIG. 2) is separated from the wall of the wellbore (2 in FIG. 2) by a small amount, referred to as the "standoff" effect. The response where the housing 10A is in contact wall of the wellbore (no standoff) is shown at curve 70. The response of the instrument 10 where there is standoff of 0.25 and 0.5 inches is shown, respectively, at curves 72 and 74. The response of the invention is comparable to prior art thermal neutron devices using a steady-state source.

Figure 9:
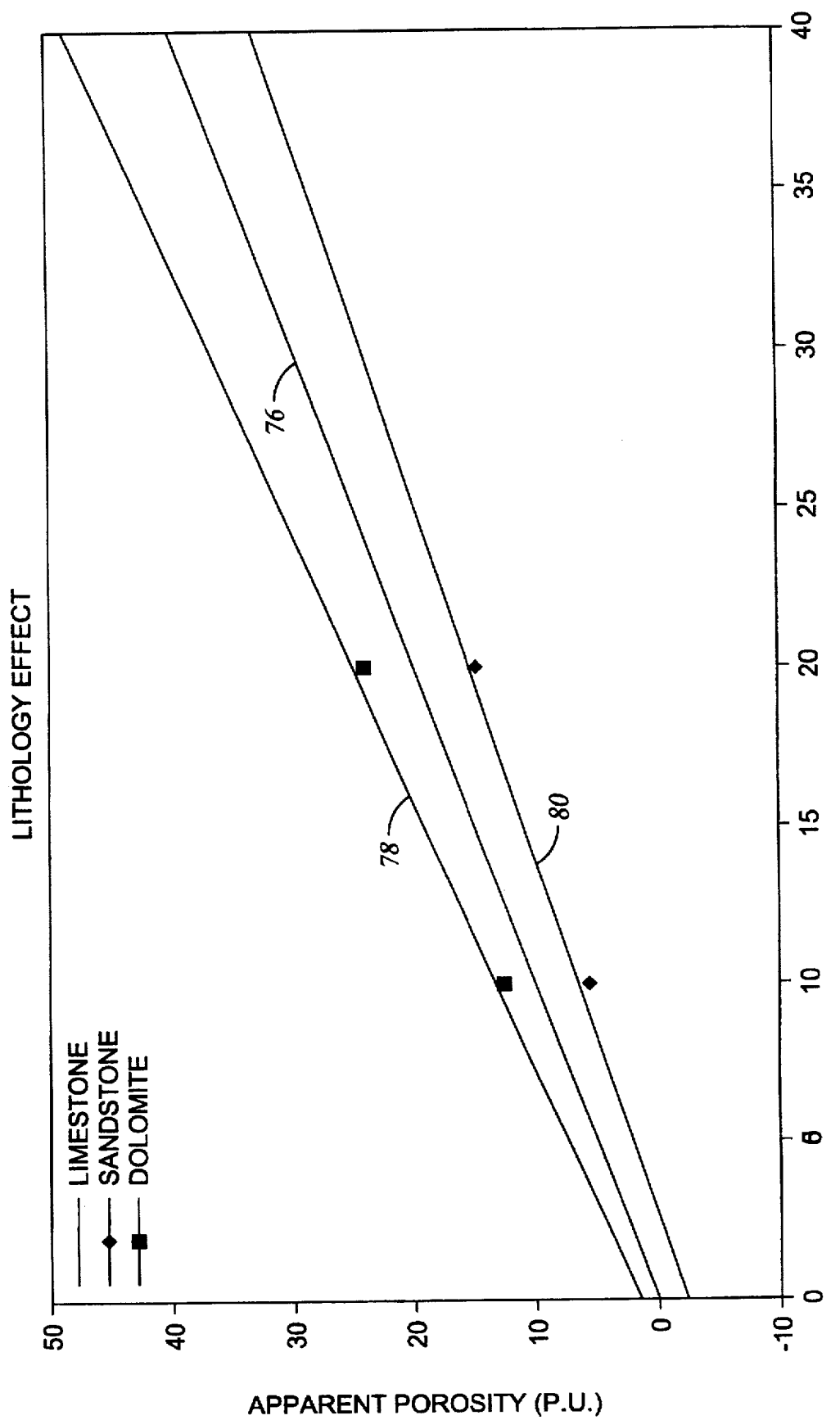
FIG. 9 shows a graph of the expected variation in response of the invention as a result of varying composition of the earth formations.

FIG. 9 shows a graph of the expected response of the instrument 10 as a result of differences in the material composition (lithology) of the earth formation (4 in FIG. 2). Neutron porosity devices are typically calibrated so that their responses substantially represent the correct fractional pore volume when operated within limestone (calcium carbonate) formation having fresh water filled pore spaces. This response is shown in FIG. 9 at curve 76. The apparent porosity response of the instrument in dolomite (calcium-magnesium carbonate) formations is shown at curve 78. The instrument 10 response in a sandstone formation (primarily composed of quartz [silicon dioxide]) formations is shown at curve 80. An interesting artifact of the construction of the instrument 10 is the apparent response in dolomite formations. Prior art thermal neutron devices typically exhibit small differences between "clean" limestone (substantially pure calcium carbonate) and "clean" dolomite (substantially pure calcium-magnesium carbonate) responses because of the lower energy neutrons (4.5 MeV approximately) from the steady-state source. The term "clean" as used herein refers to a substantial absence of thermal neutron absorbers such as gadolinium, boron and selenium as may occur in some earth formation materials such as clay or shale. For the prior art instruments, dolomite would have a shorter neutron slowing down length than limestone, but limestone has a larger neutron capture cross-section. These two effects tend to cancel each other in the response of prior art thermal neutron devices. In the invention, however, the 14 MeV energy of the neutrons emanating from the accelerator source (3 in FIG. 2) results in a reduction of the "cancellation" effect of the dolomite slowing down length. The response of the invention can be observed as a substantial difference between limestone and dolomite responses at high porosities. Correction for the apparent effect of formation lithology on the response of the instrument 10 can be programmed into the surface electronics (13 in FIG. 2) or in any other device used to calculate porosity from the count rates of the detectors 6, 8.

Figure 11A:
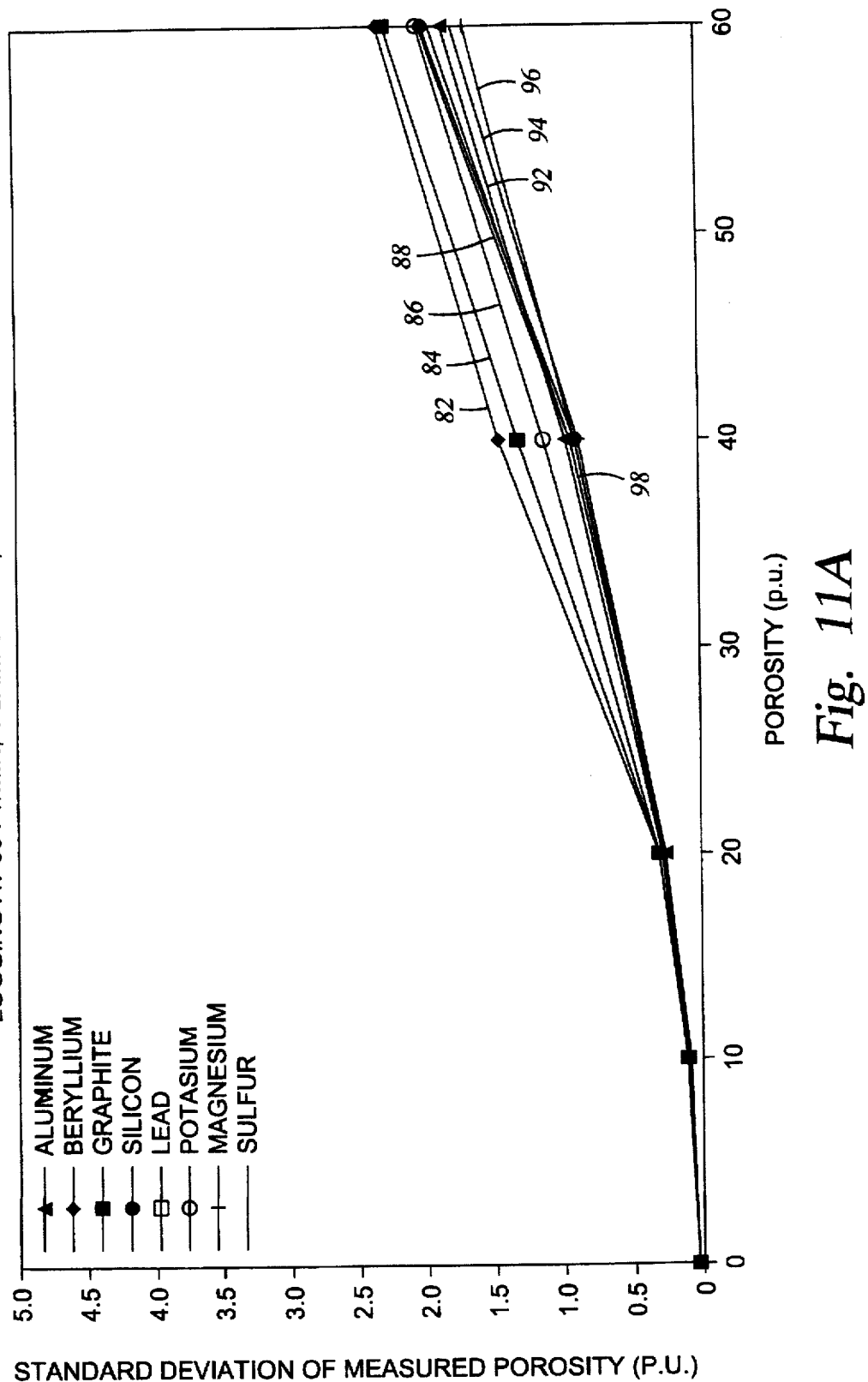
FIGS. 11A–11C show graphs of the expected statistical precision of the instrument of the invention for a number of various materials used for the scattering insert.

As previously explained, materials other than aluminum may be used for the scattering insert (15 in FIG. 3). Monte Carlo simulations were performed for various materials used as the scattering insert, and the expected response of the instrument using each of these various materials for the scattering insert 15 can be observed by referring to FIGS. 11A–11C and 12A–12C. FIG. 11A shows a graph of the expected statistical precision of the instrument 10 for some of the scattering insert materials which exhibit the best overall statistical precision. Curve 92 shows the response for an aluminum scattering insert. Curves 82, 84 and 88 respectively show the responses for beryllium, graphite and silicon. Curves 94, 86, 98 and 96, respectively, show the responses for lead, potassium, magnesium and sulfur. Each of these materials exhibits an expected statistical precision of less than about 1.0 porosity units (p.u.) statistical error at 30 p.u. porosity, this value generally accepted as being a practical upper limit for commercial use of a neutron porosity instrument.

Figure 11B:
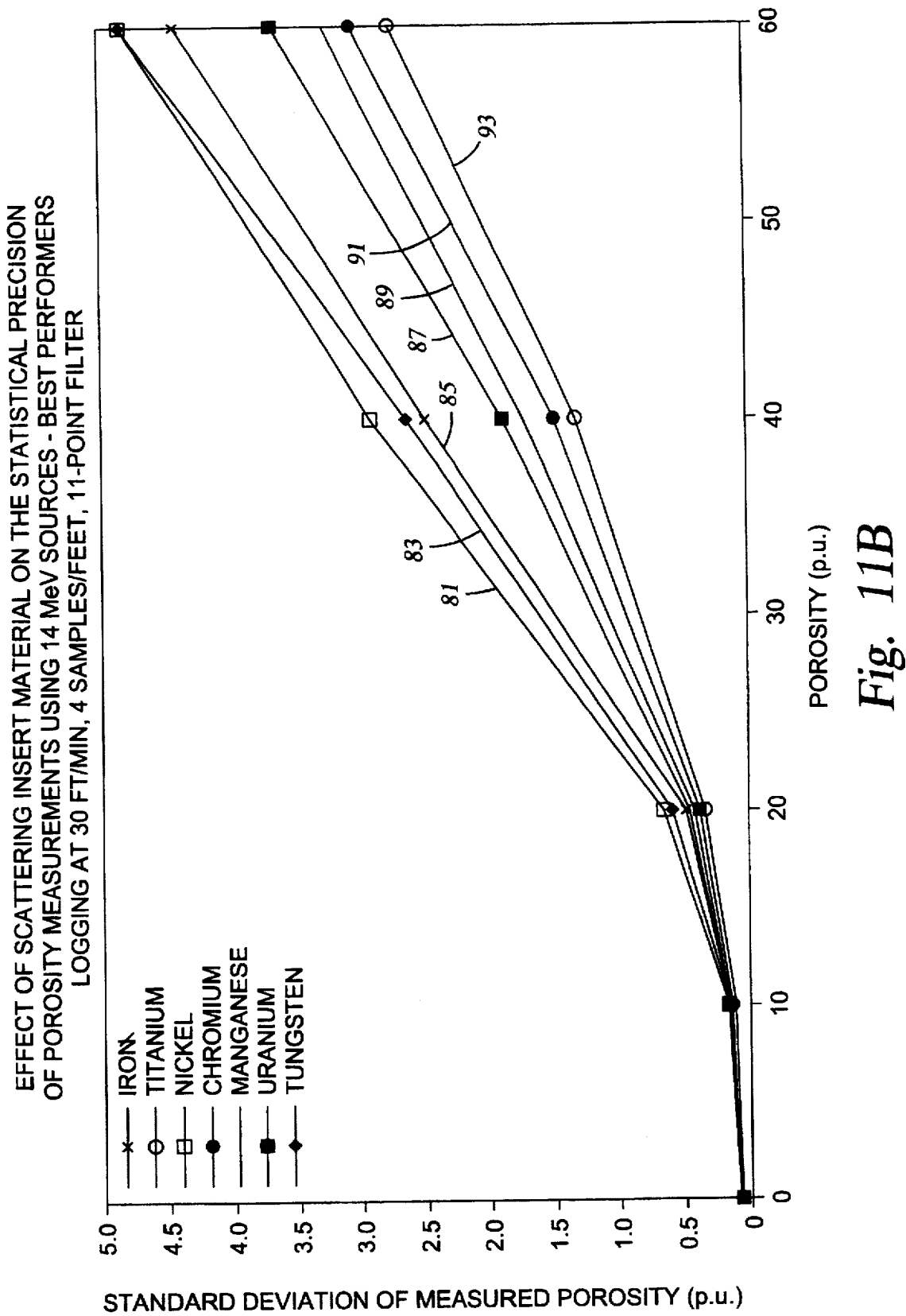

Other metals were also simulation tested for use as the scattering insert. The results of such tests are shown in FIG. 11B. These results are shown by curves 89 (iron), 93 (titanium), 81 (nickel), 91 (chromium), 85 (manganese), 87 (uranium) and 83 (tungsten). Only chromium and titanium exhibit statistical precision within the previously stated standard.

Figure 11C:
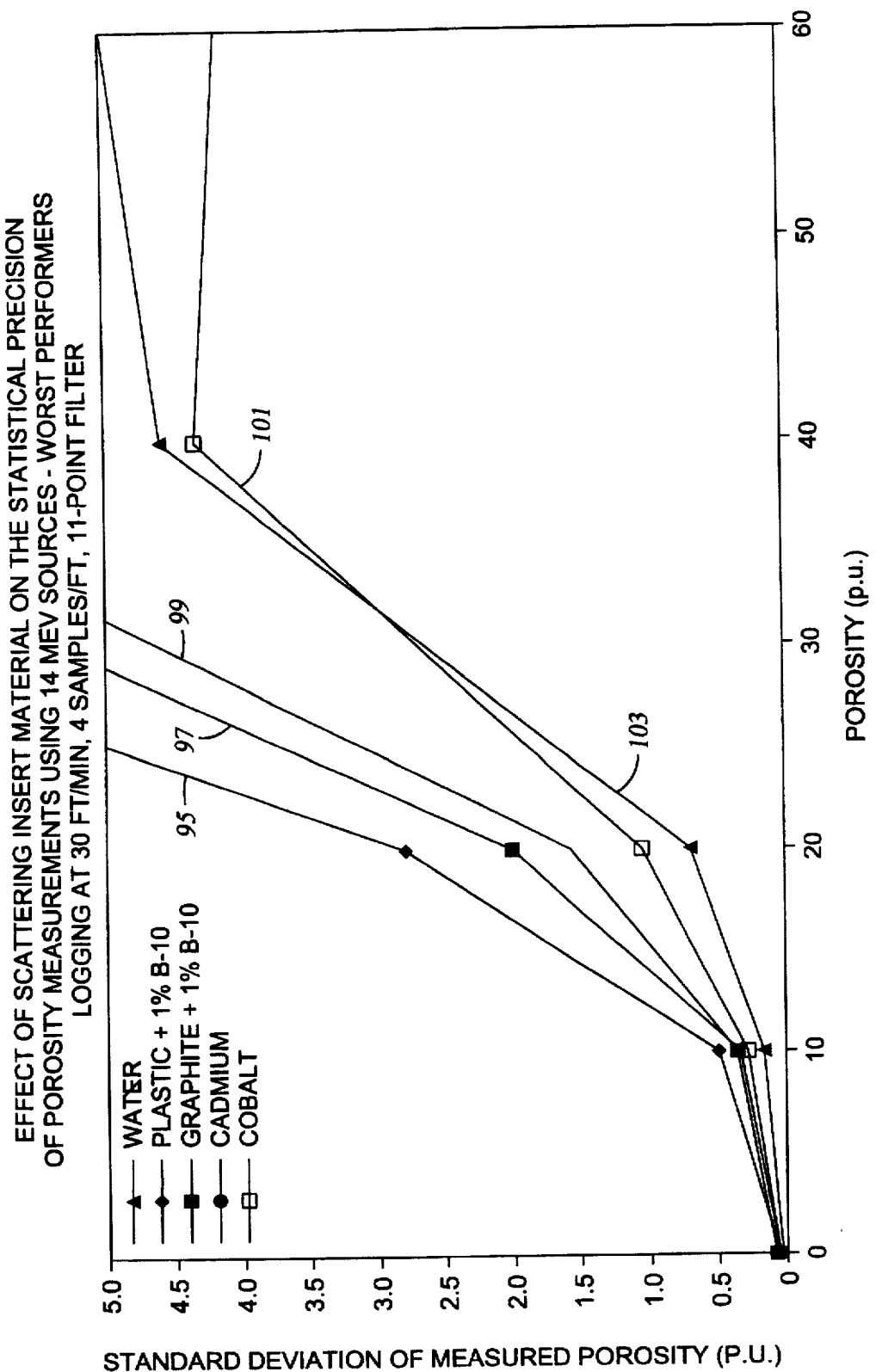

Materials which do not provide acceptable statistical precision when used for the scattering insert were also simulation tested and the results of such tests can be observed in FIG. 11C. The expected responses are shown by curves 103 (water), 95 (plastic plus 1% boron-10), 97 (graphite plus 1% boron-10), 99 (cadmium) and 101 (cobalt). A material suggested in the prior art for use as a "shield" which is located in substantially the same position as the scattering insert of this invention is described in U.S. Pat. No. 3,621,255 issued to Schwartz. This "suitable" material disclosed by Schwartz includes a combination of graphite and boron. The expected response of a scattering insert according to the invention using graphite plus 1 percent boron-10 can be observed at curve 97. The material suggested by Schwartz provides the instrument with unacceptable statistical precision at all porosity values above about 12 percent, and so is not suitable for the scattering insert of the instrument of this invention.

Figure 12A:
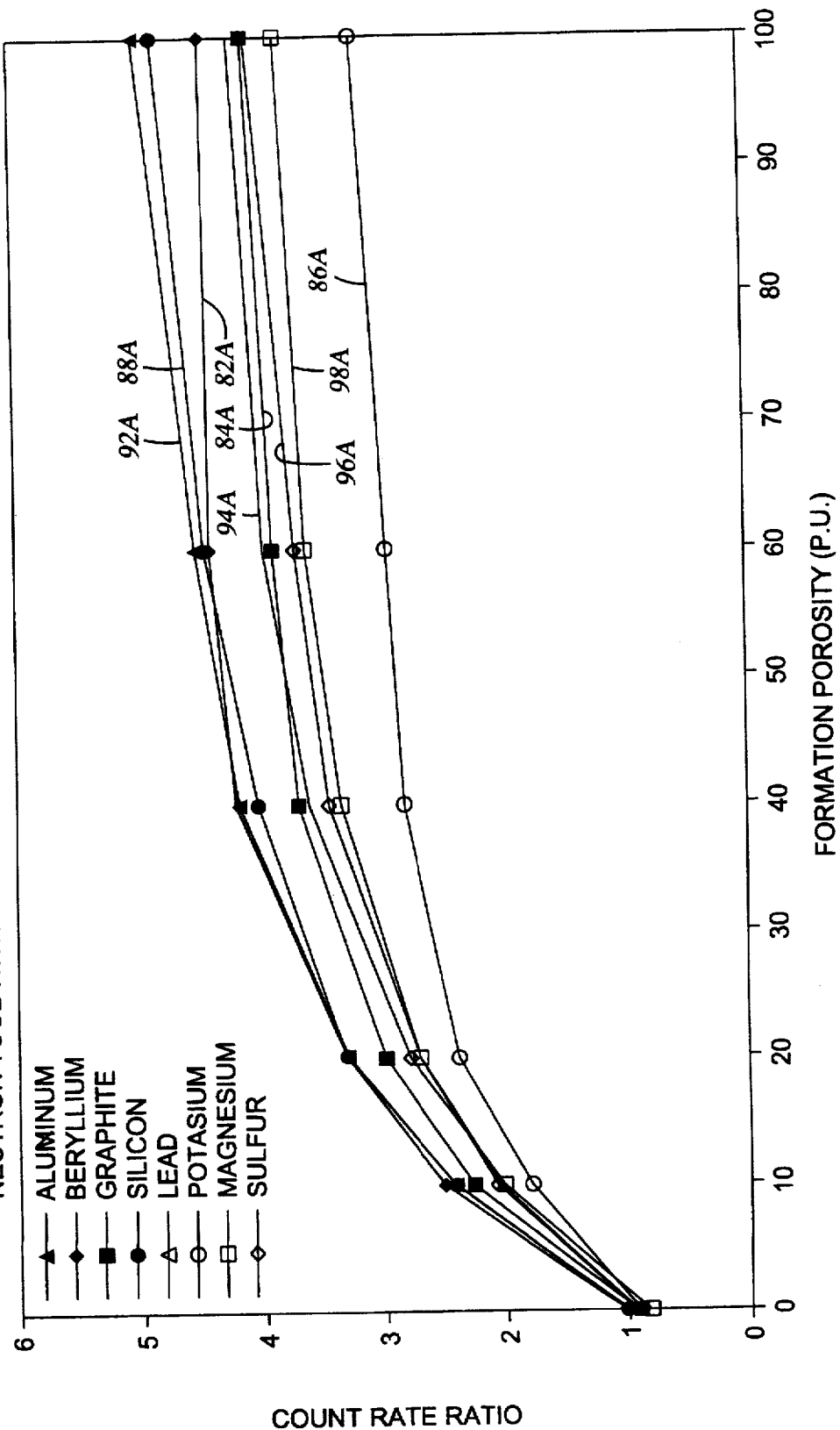
FIGS. 12A–12C show graphs of the expected porosity sensitivity of the instrument of the invention for a number of various materials used for the scattering insert.
Figure 12B:
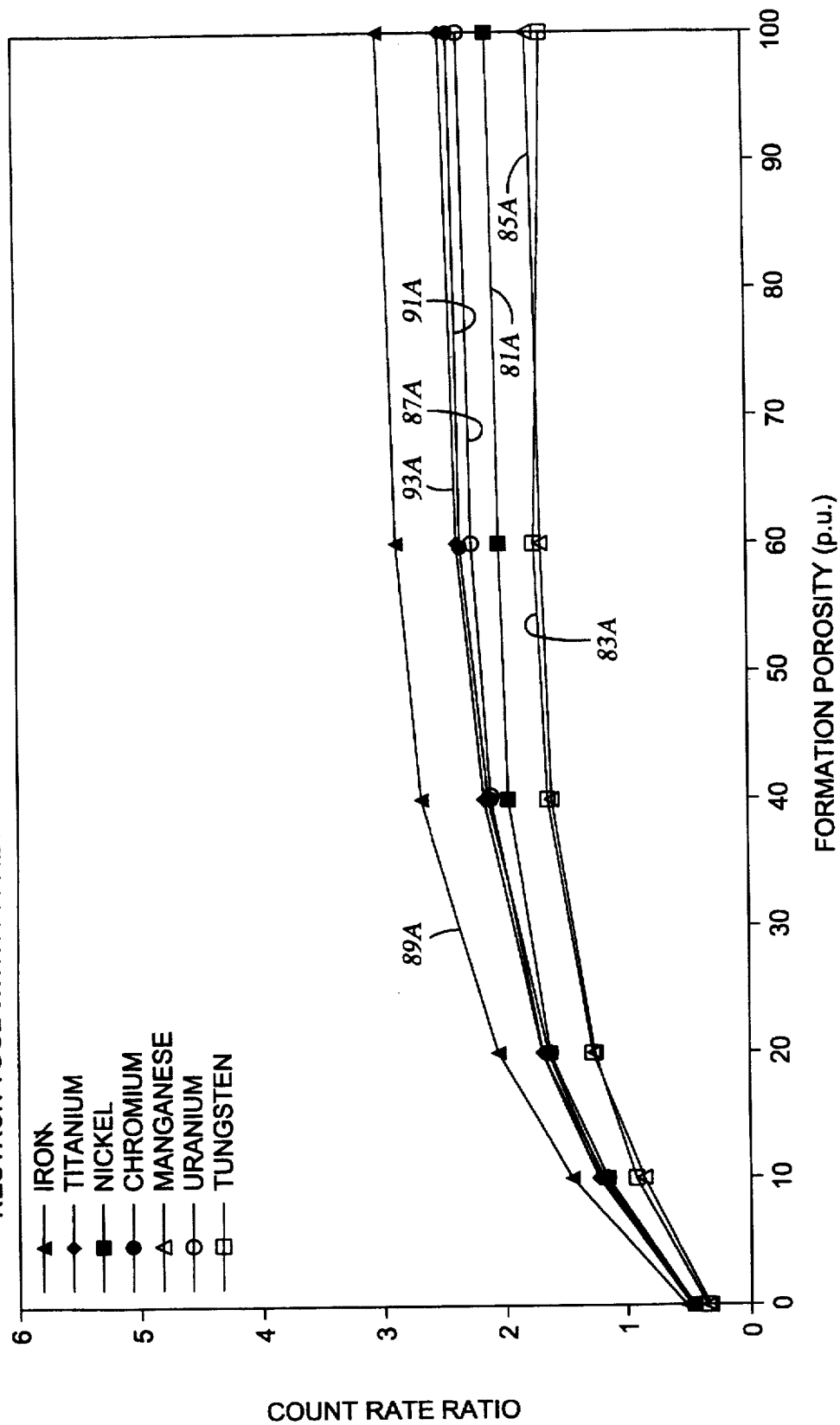
Figure 12C:
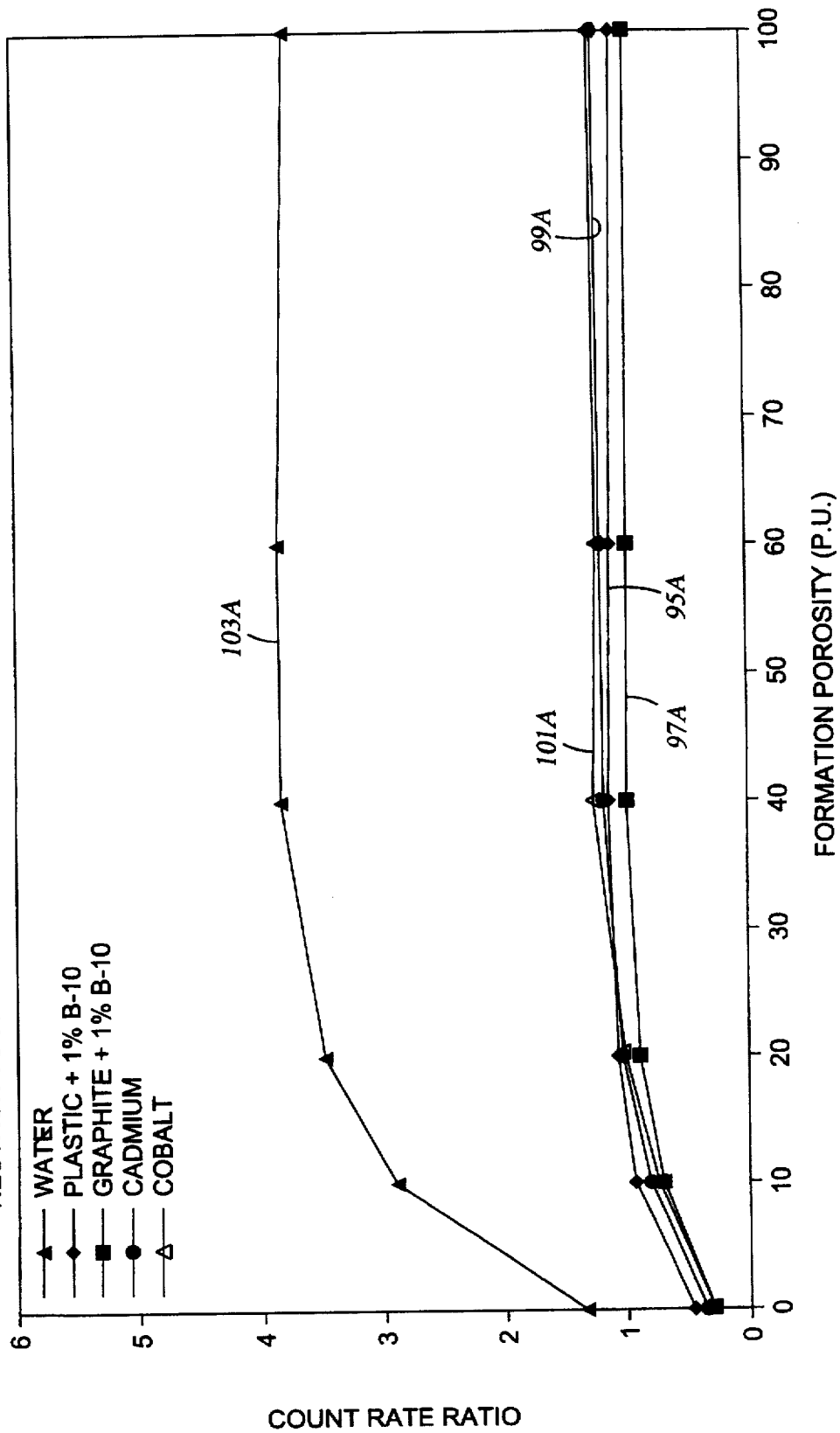

FIGS. 12A–12C show the simulated porosity sensitivity of the instrument using the same materials whose expected statistical precision values are shown in FIGS. 11A–11C. In FIG. 12A, curves for count rate ratio with respect to porosity are shown for aluminum at 92A, silicon at 88A, beryllium at 82A, graphite at 84A, lead at 94A, potassium at 86A, magnesium at 98A and sulfur at 96A.

The second group of metals whose results are shown in FIG. 11B have their expected porosity sensitivities shown in FIG. 12B at 89A (iron), 93A (titanium), 81A (nickel), 91A (chromium), 85A (manganese), 87A (uranium) and 83A (tungsten). Most of these materials exhibit substantially less porosity sensitivity than do the materials shown in FIG. 12A, and substantially all of them exhibit almost no porosity sensitivity above about 40 p.u.

The group of materials described as providing the instrument with unacceptable statistical precision have their expected porosity sensitivities shown in FIG. 12C. These are shown by curves 103A (water), 95A (plastic plus 1% boron-10), 97A (graphite plus 1% boron-10), 99A (cadmium) and 101A (cobalt). These materials exhibit substantially zero porosity sensitivity at porosity values above about 20 p.u. Particular reference is made to the porosity sensitivity of the instrument using a scattering insert made from 1 percent boron-10 doped graphite as shown at curve 97A. U.S. Pat. No. 3,621,255 issued to Schwartz shows a neutron porosity instrument similar in configuration to the instrument of this invention. Graphite plus percent boron is suggested as a suitable material to interpose between the neutron source and the near detector in the Schwartz '255 patent. The results shown in FIGS. 11C and 12C suggest that this material is entirely unsuitable for the scattering insert (15 in FIG. 2) of this invention.

DESCRIPTION OF AN ALTERNATIVE EMBODIMENT

As previously explained, it is contemplated that the instrument 10 can include one or more additional detectors which are primarily sensitive to epithermal neutrons. The epithermal neutron detectors can be provide an additional measurement corresponding to formation porosity. Measurement of epithermal neutron porosity, using an accelerator type source, is known in the art. See for example U.S. Pat. No. 4,122,340 issued to Schultz et al, or U.S. Pat. No. 5,581,079 issued to Mickael, entitled "Epithermal Neutron Porosity Measurement Apparatus and Method Corrected for Borehole Standoff and Lithology" and assigned to the assignee of this invention. These references, however, are not to be construed as an exhaustive representation of arrangements of epithermal neutron porosity measurement systems which can be included with the thermal neutron porosity measurement system of the present invention. The timing (frequency) and duration of the bursts of neutrons emanating from the source (3 in FIG. 3), as previously described, can be adjusted to accommodate inclusion of the epithermal neutron detectors in an instrument adapted to measure both epithermal neutron porosity and thermal neutron porosity.

Figure 10:
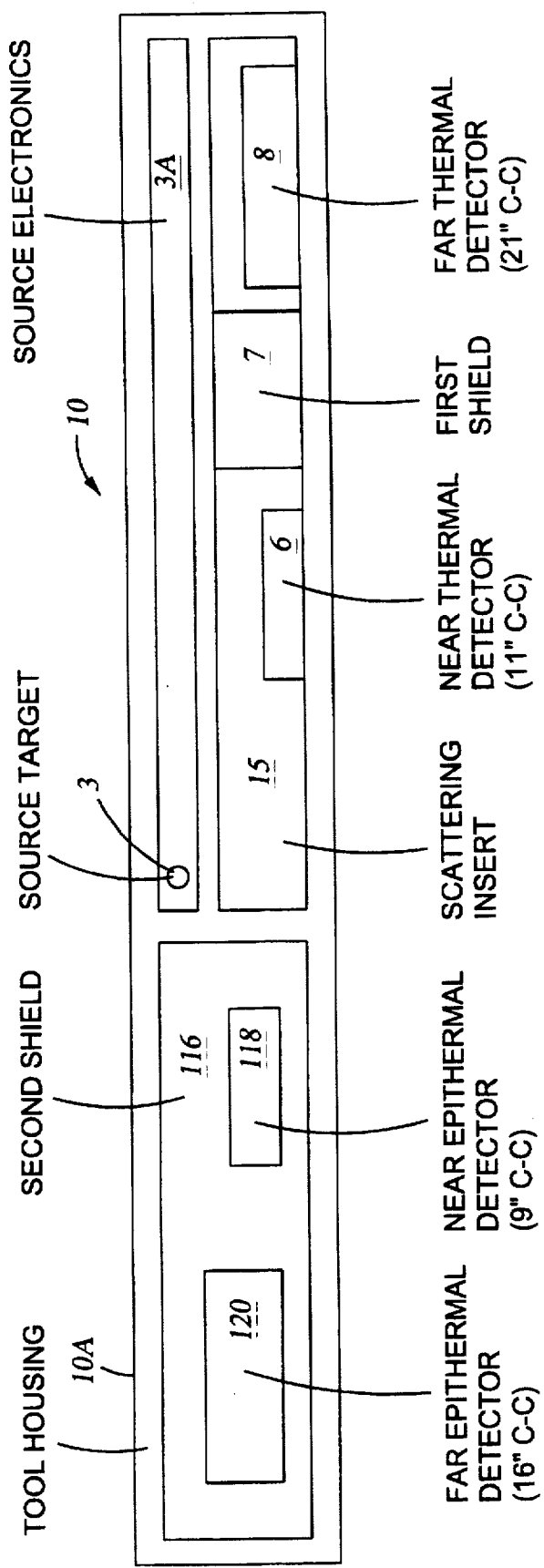
FIG. 10 shows an alternative embodiment of the invention including epithermal neutron detectors.

An arrangement for detectors which can be used to provide measurements of the epithermal neutron porosity is shown in FIG. 10. The instrument housing 10A in FIG. 10 can be similar in construction to the housing shown in FIG. 3, the difference being that the housing 10A in FIG. 10 can be axially extended past the source 3 to provide space for near 118 and far 120 epithermal neutron detectors and for a suitable shield (shown as second shield 116). Suitable epithermal detectors for use in this type of instrument 10 are described, for example, in U.S. Pat. No. 5,581,079 issued to Mickael. The arrangement of the epithermal neutron detectors 118, 120 and of the neutron shielding material 116, can be similar to the arrangement described, for example, in U.S. Pat. No. 5,532,481 issued to Mickael. Methods for counting epithermal neutrons after detection and conversion of the counts into the measurements of epithermal neutron porosity are also described in the Mickael '481 patent.

The remainder of the instrument 10 in FIG. 10 can include the thermal neutron detectors 6, 8, the source 3 and its associated circuits 3A, the scattering insert 15 and the shield (shown as first shield 7) as described in the first embodiment of this invention.

The invention provides a means for measuring the thermal neutron porosity of earth formations which has substantially similar response to prior art thermal neutron devices using steady-state neutron sources, while providing the safety benefit of a neutron source which is substantially non-radioactive until disposed in the wellbore and is energized by the system operator.

Those skilled in the art will readily devise other embodiments of the invention which do not depart from the spirit of the invention as described herein. Accordingly, the scope of the invention should be limited only by the attached claims.

What is claimed is:

1. An apparatus for measuring thermal neutron porosity of earth formations penetrated by a wellbore, comprising:

a selectively controllable source of high-energy neutrons;

a near detector axially spaced apart from said source, said near detector primarily sensitive to thermal neutrons;

a far detector axially spaced apart from said source so that said near detector is axially disposed between said source and said far detector, said far detector primarily sensitive to thermal neutrons;

a counter for determining numbers of neutrons detected substantially continuously at each one of said near and far detectors;

a neutron shield disposed between said near detector and said far detector, said shield comprising a material which moderates and absorbs neutrons; and a neutron scattering insert disposed between said source and said near detector, said insert consisting of a material selected from the group consisting of aluminum, beryllium, graphite, silicon, potassium, lead, magnesium and sulfur.

2. The apparatus as defined in claim 1 wherein said near detector and said far detector comprise helium proportional counters.

3. The apparatus as defined in claim 1 wherein said source comprises an accelerator source.

4. The apparatus as defined in claim 1 wherein said shield comprises boron-10 doped plastic.

5. The apparatus as defined in claim 1 further comprising:

at least one epithermal neutron detector axially spaced apart from said source; and means for calculating said porosity of said earth formation from counts of epithermal neutrons detected by said at least one epithermal neutron detector.

6. A method for thermal neutron porosity logging of earth formations penetrated by a wellbore, comprising:

irradiating said formation with bursts of high-energy neutrons from a source;

scattering said high-energy neutrons travelling substantially along said wellbore and not entering said earth formation, said step of scattering performed by an insert consisting of a material selected from the group consisting of aluminum, beryllium, graphite, silicon, lead, potassium, magnesium and sulfur, said scattering performed axially between said irradiating and a first location axially spaced apart from said irradiating;

detecting thermal neutrons from said earth formation at said first location substantially continuously;

shielding thermal neutrons from travelling axially between said first location and a second location axially further spaced apart from said irradiating than said first location, said shielding performed by a material which moderates and absorbs neutrons; and detecting thermal neutrons from said earth formation at said second location substantially continuously.

7. The method as defined in claim 6 further comprising calculating a neutron porosity by determining a ratio of numbers of said detected thermal neutrons from said first location with respect to numbers of said thermal neutrons detected at said second location.

8. The method as defined in claim 6 wherein said high-energy neutrons have an average energy of about 14 MeV.

9. The method as defined in claim 6 wherein said first location is about 11 inches from said source.

10. The method as defined in claim 6 wherein said second location is about 21 inches from said source.

11. The method as defined in claim 6 further comprising: detecting epithermal neutrons at a third location axially spaced apart from said source; and calculating said porosity from counts of said epithermal neutrons detected at said third location.

12. The method as defined in claim 6 wherein said first location and said second location are proximal to a wall of said wellbore.

13. A method for thermal neutron porosity logging of earth formations penetrated by a wellbore, comprising:

irradiating said formation with bursts of high-energy neutrons from a source;

scattering said high-energy neutrons travelling substantially along said wellbore and not entering said earth formation, said step of scattering performed by an insert consisting of a material selected from the group consisting of aluminum, beryllium, graphite, silicon, lead, potassium, magnesium and sulfur, said scattering performed axially between said irradiating and a first location axially spaced apart from said irradiating;

detecting thermal neutrons from said earth formation at said first location substantially continuously;

shielding thermal neutrons form travelling axially between said first location and a second location axially further spaced apart from said irradiating than said first location, said shielding performed by a material which moderates and absorbs neutrons; and detecting thermal neutrons from said earth formation at said second location, whereby thermal neutron porosity is calculated from numbers of said thermal neutrons detected at said first and said second locations.

14. The method as defined in claim 13 wherein the calculating of said neutron porosity comprises determining a ratio of said numbers of said detected thermal neutrons from said first location with respect to said numbers from said second location.

15. The method as defined in claim 13 wherein said high-energy neutrons have an average energy of about 14 MeV.

16. The method as defined in claim 13 further comprising:

detecting epithermal neutrons at a third location axially spaced apart from said source; and calculating said porosity from counts of said epithermal neutrons detected at said third location.

17. The method as defined in claim 13 wherein said first location and said second location are proximal to a wall of said wellbore.

* * * * *